United States Patent [19]

Whitney et al.

[11] 4,068,870

[45] Jan. 17, 1978

[54] FLEXIBLE HOSE COUPLING

[75] Inventors: John Kimball Whitney, Orchard Park; Allan Hugh Cosgrove, Eggertsville; Roland Edward Flick, West Seneca, all of N.Y.

[73] Assignee: Gaymar Industries Incorporated, Orchard Park, N.Y.

[21] Appl. No.: 673,275

[22] Filed: Apr. 2, 1976

[51] Int. Cl.² ............................................. F16L 47/00
[52] U.S. Cl. ................................... 285/320; 285/423; 285/DIG. 22
[58] Field of Search ........ 285/320, 319, 423, DIG. 22

[56] References Cited

U.S. PATENT DOCUMENTS

| | | | |
|---|---|---|---|
| 1,209,374 | 12/1916 | Andreolli | 285/320 X |
| 2,281,633 | 5/1942 | Stitzer | 285/320 X |
| 2,494,774 | 1/1950 | Messick | 285/320 X |
| 2,664,303 | 12/1953 | Mansfield | 285/319 |
| 3,245,703 | 4/1966 | Manly | 285/DIG. 22 |
| 3,250,551 | 5/1966 | Draudt | 285/DIG. 22 |
| 3,394,954 | 7/1968 | Sarns | 285/319 |
| 3,712,646 | 1/1973 | Bergougnoux | 285/319 X |

*Primary Examiner*—Thomas F. Callagham
*Attorney, Agent, or Firm*—William H. McNeill

[57] ABSTRACT

A coupling for hose comprises male and female members one of which carries a locking device for engaging a surface on the other member. The locking device is carried by a pair of opposed hinged arms and comprises a semi-circular unit containing an over-center, semi-circular aperture dimensioned to encompass a specific area on the other member.

4 Claims, 6 Drawing Figures

FLEXIBLE HOSE COUPLING

BACKGROUND OF THE INVENTION

This invention relates to couplers for joining flexible hoses, particularly, fluid carrying hoses employed with medical apparatus. Such apparatus can include, but is not limited to, air mattresses and water beds. The couplers can also be employed with apparatus for draining or introducing body fluids. When used in any of the above applications it is necessary that such couplers be rugged; provide a good fluid seal; be simple to use; and be easy to connect and disconnect.

OBJECTS AND SUMMARY OF THE INVENTION

It is, therefore, an object of the invention to provide an enhanced hose coupler.

It is yet another object of the invention to provide a hose coupler that is simple to use and rugged in operation, thus leading to a long life.

It is still another object of the invention to provide a hose coupler employing simple means for connecting and disconnecting.

These objects are accomplished in one aspect of the invention by the provision of a hose coupler that comprises a male member and a female member. The male member comprises a tubular body having a first end formed to engage a hose and a second end formed to telescopically couple with the female member. The female member also has a body with a first end formed to engage a hose and a second end formed to receive said male member. Releasable locking means are formed on one of the members to engage a surface on the other of the members. The locking means comprises a locking device carried by a pair of opposed, hinged arms, thus making the locking device pivotable into and out of locking engagement and providing easy one handed operation.

DESCRIPTION OF THE PREFERRED EMBODIMENTS

For a better understanding of the present invention, together with other and further objects, advantages and capabilities thereof, reference is made to the following disclosure and appended claims in conjunction with the above-described drawings.

Figure 1:
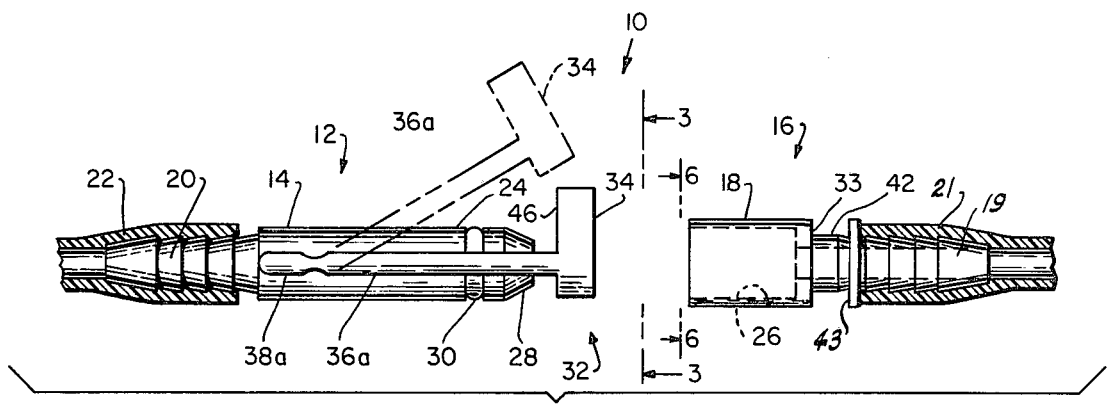
FIG. 1 is an exploded elevational view of the coupler of the invention, with some parts in section and some in phantom.

Referring now to the drawings with greater particularity, there is shown in FIG. 1 a coupling 10 for flexible hose which comprises a male member 12 having an elongated tubular body 14 provided with an axial bore, not shown, and a female member 16 which has a body 18.

The male member 12 has a first end 20 which is formed to engage a flexible hose 22 by frictional engagement with the inside diameter of the hose. The frictional engagement can be obtained by providing first end 20 with a plurality of serrated ribs, as is conventional in the art.

A second end 24 of male member 12 is formed to telescopically couple with an internal bore 26 of female member 16. To facilitate easy entry of the second end 24 of male member 12 into the female member 16, the end 24 can be tapered, as at 28. One or more sealing gaskets 30 can be provided adjacent end 24 to aid in forming a fluid tight seal.

Figures 5, 6:
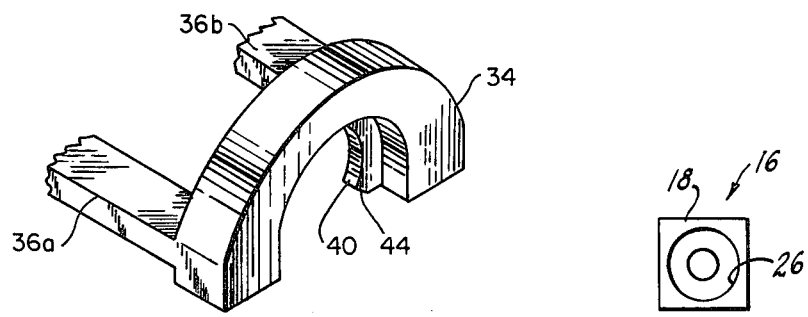
FIG. 5 is a perspective view of the locking device.
FIG. 6 is an end view of the female member taken along the line 6—6 of FIG. 1.

The female member 16 has the internal bore 26 formed in body 18 which is also provided with an end 19 for frictionally engaging the inside diameter of a hose 21. The outside configuration of body 18 is preferably non-circular, such as shown in FIG. 6, for reasons to be explained hereinafter.

A releasable locking means 32 is formed on one of the members, in this case the male member 12; however, it is to be understood that this is exemplary only, and that the locking means 32 could also be carried by the female member 16. The locking means 32 is formed to engage a surface 33 on the other member and comprises a locking device 34 carried by the distal ends of a pair of opposed, hinged arms 36a and 36b which are attached, at their proximal ends 38a and 38b opposite the locking device, to the body of the appropriate member. The releasable locking means 32, including the locking device 34 and the arms 36a and 36b are made from a resilient or deformable material, such as polyethylene or polypropylene, which is also preferably the material of the member to which they are attached. The member, such as male member 12, and the releasable locking means 32 can thereby be mold as one piece.

Figure 3:
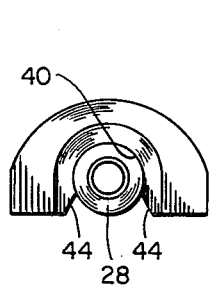
FIG. 3 is an end view of the locking device taken along the line 3—3 of FIG. 1.
Figure 4:
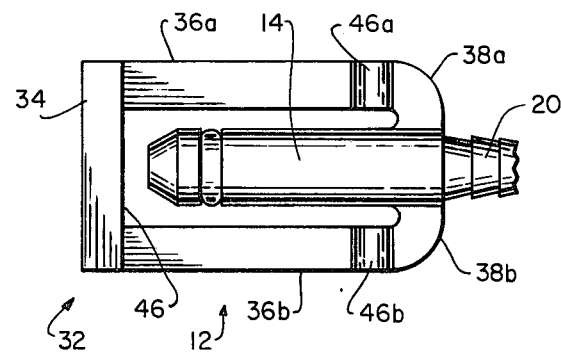
FIG. 4 is a plan view of the male member.

The locking device 34 (shown in detail in FIGS. 3 and 5) comprises a semi-circular unit containing an over-center, semi-circular aperture 40 which is dimensioned to encompass a specific area 42 on the other member, in this case female member 16. The specific area 42 is adjacent to locking surface 33. Also adjacent to the specific area 42, but opposite locking surface 33 is a projecting stop 43, which prevents the hose 21 from being pushed too far onto the end 19 and interfering with the closure of the locking device 34.

Angled surfaces 44 lead into aperture 40, thus facilitating engagement with specific area 42, which also is aided by the deformable material of the locking device.

Figure 2:
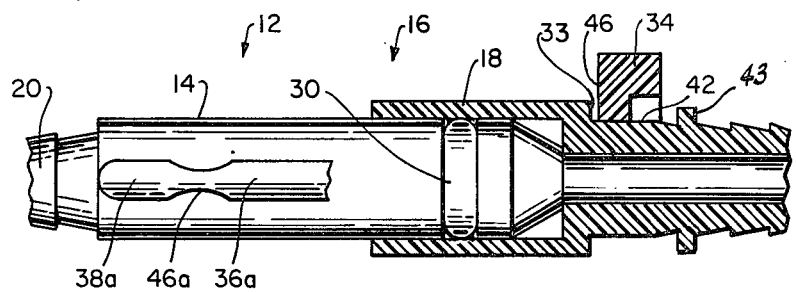
FIG. 2 is an elevational view of the coupler of the invention in its functional, joined position with some parts in section.

The partial sectional view of FIG. 2 illustrates the coupler 10 in its mated position. The aperture 40 partially surrounds the specific area 42 and the rear surface 46 of locking device 34 abuts locking surface 33 making a secure connection. The greater area of connective contact afforded by this construction gives decided advantages over prior art structures. As mentioned above, the outer configuration of body 18 of female member 16 is preferably non-circular, and a square cross-section is ideal. This construction prohibits an operator from closing locking device 34 over the body 18 in the event that the male member 12 is not sufficiently seated within internal bore 26. When body 18 is tubular such a condition is a definite possibility and this occurrence could cause such a deformation in locking device 34 as to render it unusable.

To disengage the locking device 34, it is only necessary to employ finger or thumb pressure upwardly to the locking device 34, raising it to the position shown in phantom lines in FIG. 1. The members are then separated by opposed axial movement.

The pivotal movement of the locking device 34 is aided by the hinges 46a and 46b, which are formed by thinned areas in the arms 36a and 36b.

The coupler of this invention provides a simple and unique structure that is easy to use and fabricate. The area of coverage obtained by the locking surface 33 and the rear surface 46, together with the circumferential coverage afforded by aperture 40 about specific area 42 provides a rugged unit having a high degree of reliability.

While there have been shown and described what are at present considered the preferred embodiments of the invention, it will be apparent to those skilled in the art that various changes and modifications may be made herein without departing from the scope of the invention as defined by the appended claims.

What is claimed is:

1. A coupling for flexible hose comprising: a male member and a female member; said male member having a body with a first end formed to engage a hose and a second end formed to telescopically couple internally with a chamber in said female member; said female member having a body with a first end formed to engage a hose and a second end containing said chamber formed to receive said second end of said male member therein, said chamber having a circular cross-section; the outer configuration of said second end of said female member being non-circular; and releasable locking means formed on said male member to engage a specific area on said female member, said specific area lying between said first and second ends of said female member and being immediately adjacent a locking surface formed by an edge of said non-circular body, said locking means comprising a locking device carried by a pair of opposed, hinged arms, said locking device thus being pivotable into and out of locking engagement said locking device being formed of resilient material and including a semi-circular unit comprising an over-center-semi-circular aperature dimensioned to encompass a specific area of said other member adjacent said locking surface, said semi-circular unit and said non-circular second end of the female member being constructed to prevent closing said semi-circular unit over said non-circular second end in the event the male member is not sufficiently seated within said chamber.

2. The coupling of claim 1 wherein said locking device includes angled surfaces leading into said over-center aperture.

3. The coupling of claim 1 wherein the distal ends of said arms carry said locking device and the proximal ends of said arms, which are formed on said member, are formed to provide said hinges.

4. The coupling of claim 3 wherein said hinges are formed by thinned areas in said arms.

* * * * *